(12) United States Patent
Hariharan

(10) Patent No.: US 6,677,298 B2
(45) Date of Patent: Jan. 13, 2004

(54) REGULATORS OF PPARδ (β) AND THEIR USE IN THE TREATMENT OF OBESITY AND INSULIN RESISTANCE

(75) Inventor: Narayanan Hariharan, Richboro, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/909,098

(22) Filed: Jul. 19, 2001

(65) Prior Publication Data

US 2002/0042359 A1 Apr. 11, 2002

Related U.S. Application Data

(60) Provisional application No. 60/219,956, filed on Jul. 20, 2000.

(51) Int. Cl.[7] ............................................. A01N 61/00
(52) U.S. Cl. ....................................................... 514/1
(58) Field of Search ........................... 514/369, 2, 376, 514/309

(56) References Cited

U.S. PATENT DOCUMENTS

| | | | |
|---|---|---|---|
| 5,487,992 A | 1/1996 | Capecchi et al. | |
| 5,571,696 A | 11/1996 | Evans et al. | |
| 5,627,059 A | 5/1997 | Capecchi et al. | |
| 5,861,274 A | 1/1999 | Evans et al. | |
| 6,008,237 A | * 12/1999 | Sahoo et al. ................. | 514/369 |
| 2002/0013334 A1 | * 1/2002 | Robl et al. ................... | 514/291 |

FOREIGN PATENT DOCUMENTS

| | | |
|---|---|---|
| WO | WO97/10813 | 3/1997 |
| WO | WO97/28149 | 8/1997 |
| WO | WO 01/07066 | 2/2001 |

OTHER PUBLICATIONS

Forman BM, Chen J, Evans RM. Hypolipidemic drugs, polyunsaturated fatty acids, and eicosanoids are ligands for peroxisome proliferator–activated receptors alpha and delta. Proc Natl Acad Sci U S A. Apr. 29, 1997;94(9):4312–7.*

Henke et al. N–(2–Benzoylphenyl)–L–tyrosine PPAR-gamma agonists. 1. Discovery of a novel series of potent antihyperglycemic and antihyperlipidemic agents. J Med Chem. Dec. 3, 1998;41(25):5020–36.*

Peters, J.M. et al., Molecular and Cellular Biology, vol. 20, No. 14, pp. 5119–5128 (2000).

Kubota et al. (1999) Molecular Cell, vol. 4, 597–609.

Kliewer et al. (1994) Natl Acad Sciences, vol. 91, 7355–7359.

Berger et al. (1999) J Biol Chem, vol. 274, Issue 10, 6718–6725.

Bastie et al. (1999) J Biol Chem, vol. 274, Issue 31, 21920–21925.

Mano et al. (2000) J Biol Chem, vol. 275, Issue 11, 8126–8132.

Leibowitz et al. (2000) FEBS Letters, vol. 473, Issue 3, 333–336.

Schmidt et al. (1992) Mol Endocrinology, vol. 6, 1634–1641.

* cited by examiner

*Primary Examiner*—Karen Cochrane Carlson
*Assistant Examiner*—Sheridan Snedden
(74) *Attorney, Agent, or Firm*—Briana C. Buchholz; Christopher A. Klein

(57) ABSTRACT

Obesity is a common clinical problem in most developed nations and is also rapidly becoming a major health concern in developing nations. Overweight individuals frequently suffer from several metabolic disorders such as insulin resistance, type 2 diabetes and dyslipidemia. This invention discloses proof of principle for the role PPARδ (also known as β) plays in the development of diet-induced obesity. In accordance with the present invention, a new method for treating obesity, insulin resistance and hyperlipidemia through administration of a pharmaceutical composition containing a chemical agent that antagonizes the function of PPARδ(β) protein, decreases PPARδ(β) gene expression and or transactivation of PPARδ(β) target gene expression is disclosed. This invention also proposes that obese, insulin resistant hyperlipidemic patients can be effectively treated with a combination of a PPARδ(β) antagonist with either an anti-diabetic agent or a lipid-lowering agent (or both).

4 Claims, 6 Drawing Sheets

*Statistically significant difference, $p < 0.05$.

*Statistically significant difference, $p < 0.05$.

REGULATORS OF PPARδ (β) AND THEIR USE IN THE TREATMENT OF OBESITY AND INSULIN RESISTANCE

CROSS-REFERENCE TO RELATED APPLICATIONS

This application claims the benefit of U.S. Provisional Application No. 60/219,956, filed Jul. 20, 2000.

FIELD OF THE INVENTION

The present invention relates to a method for treating obesity, insulin resistance and dyslipidemia in mammals including humans through inhibition of PPARδ(β). This invention also relates to methods of screening for chemical entities that act to regulate PPARδ(β) activity. The invention further relates to a method of treatment of obese, insulin resistant and hyperlipidemic patients with one or more combinations of a PPARδ(β) antagonist, an anti-diabetic agent and a lipid-lowering agent.

BACKGROUND OF THE INVENTION

Obesity is a common clinical problem in most developed nations and is also rapidly becoming a major health concern in developing nations. Overweight individuals frequently suffer from several metabolic disorders such as insulin resistance, type 2 diabetes and dyslipidemia. These individuals also frequently suffer from hypertension, increased risk for cardiovascular diseases such as atherosclerosis and coronary heart disease, and osteoarthritis of the joints.

In mammals, including humans, adipocytes (fat cells) store excess energy in the form of triglycerides at times of nutritional excess (see Lowell, *Cell,* 99:239–242, 1999). During starvation, triglycerides are degraded to fatty acids in adipocytes in order to supplement nutritional and energy requirements. However, excess adiposity achieved either through recruitment of progenitor cells (pre-adipocytes) to become adipocytes (differentiation) and/or through expansion of the pre-existing adipocytes (hypertrophy), is associated with obesity (see Lowell, *Cell,* 99:239–242, 1999). Hypertrophied adipocytes have been demonstrated to produce excessive amounts of cytokines such as TNFα(which in turn act to reduce insulin receptor activity and/or response to insulin signaling in skeletal muscle and adipocytes, two major glucose utilizing tissues (see Hotamisligil, et al., *Science,* 259:87–90, 1993; Lowell, *Cell,* 99:239–242, 1999). This results in insulin resistance, reduced glucose uptake, and in some individuals type 2 diabetes. Obese individuals with insulin resistance and type 2 diabetes also frequently suffer from hyperlipidemia, atherosclerosis and cardiovascular diseases (see Rosenbaum et al., *New. Eng. J. Med.* 337:396–407, 1997).

Peroxisome Proliferator Activated Receptors (PPARs) are members of the nuclear hormone receptor family of ligand regulated transcription factors (see Willson, et al., *J. Med. Chem.,* 43:527–550, 2000). Three PPAR isoforms, PPARα, PPARγ and PPARδ, have been isolated from various mammalian species including humans. These receptors, as a class, form obligate heterodimers with their binding partner RXRα, and are activated by diet derived long chain fatty acids, fatty acid metabolites and/or by synthetic agents (see Willson, et al., *J. Med. Chem.,* 43:527–550, 2000). PPARα regulates genes in the fatty acid synthesis, fatty acid oxidation and lipid metabolism pathways (see Issenman and Green, *Nature,* 347: 645–649, 1990; Torra et al., *Current Opinion in Lipidology,* 10:151–159, 1999). The marketed PPARα agonists, such as fenofibrate and gemfibrozil, lower plasma lipids in mammals including humans (see Balfour et al., Drugs. 40:260–290, 1990; Frick et al., *New Eng. J. Med.,* 317:1237–1245; Rubins et al., *New Eng. J. Med.,* 341:410–418, 1999). PPARγ has been demonstrated to regulate pre-adipocyte recruitment and differentiation into mature adipocytes. Activators of PPARγ promote lipid storage in adipocytes and act as insulin sensitizing anti-diabetic agents (see Lehmann et al., *J. Biol. Chem.,* 270:12953–12956, 1995; Nolan et al. *New. Eng. J. Med.,* 331:1188–1193; Inzucchi et al., *New Eng. J. Med.,* 338:867–872, 1998). The role of the relatively more ubiquitously expressed PPARδ(also known as PPARβ, herein referred to as PPARδ(β)) isoform has been unclear although it is known that: (1) PPARδ(β) is present in pre- and mature adipocytes, and (2) it is activated by fatty acids and fatty acid metabolites (see Zhang et al., *Mol. Endocrinology,* 10:1457–1466, 1996; Berger et al. *J. Biol. Chem.,* 274:6718–6725, 1999; Bastie et al., *J. Biol. Chem.,* 274:21920–21925, 1999).

SUMMARY OF THE INVENTION

Accumulation of excess adipocyte tissue either through recruitment of progenitor cells to become adipocytes and/or expansion of the pre-existing adipocytes is frequently associated with obesity. Although expressed in pre- and mature adipocytes and activated by fatty acids and fatty acid metabolites, the role of PPARδ(β) in adipocyte function, adipocyte hypertrophy and or development of obesity has not been clear. The present invention demonstrates for the first time a role for PPARδ(β) in the development of diet-induced obesity.

Accordingly, one object of the present invention is to provide a method for treating obesity in a mammal, including human, comprising administering to the mammal in need of such treatment a therapeutically effective amount of a compound or combination of compounds that inhibits or modulates PPARδ(β) activity.

Another object of the present invention provides a method for treating obesity, insulin resistance and dyslipidemia in a mammal, including human, comprising administering to the mammal in need of such treatment a therapeutically effective any combination of two or more of the following compounds: a compound or combination of compounds that inhibit PPARδ(β) activity, an anti-diabetic compound, and a lipid-lowering agent.

Another object of the present invention provides a method for treating osteoarthritis in a mammal, including human, comprising administering to the mammal in need of such treatment a therapeutically effective amount of a compound or combination of compounds that inhibits or modulates PPARδ(β) activity.

Another object of the present invention provides a method for screening for compounds that inhibits or regulate PPARδ (β) activity.

Another object of the present invention provides a pharmaceutical composition for the treatment of obesity, insulin resistance and/or dyslipidemia, comprising: a pharmaceutically acceptable carrier and a therapeutically effective amount of a compound or combination of compounds that inhibit or regulate PPARδ(β) activity.

In this study mice were maintained on a high fat/high sucrose diet for 16 weeks, body weights were monitored every two weeks. PPARδ(β)+/+, wild type mice with two functional copies of the PPARδ(β) gene and PPARδ(β)+/−, heterozygous knockout mice with one PPARδ(β) gene copy inactivated were used in this study.

Figure 2:
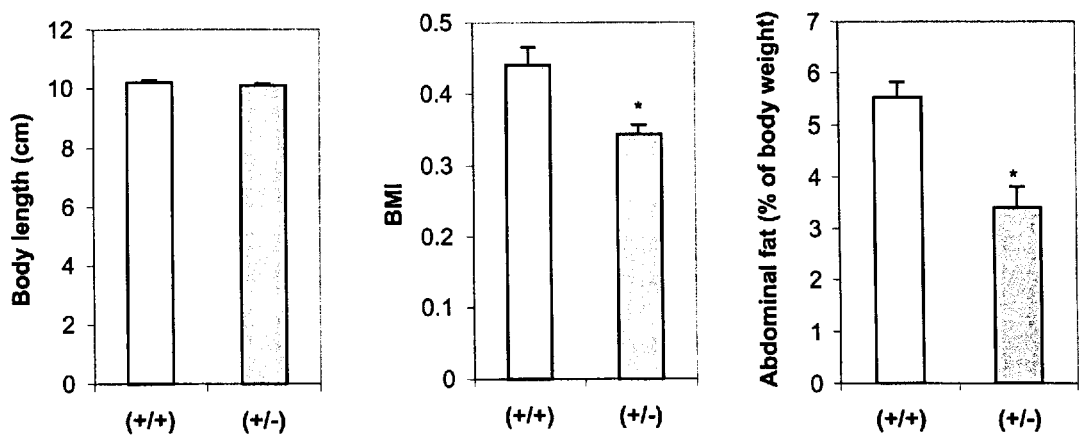

FIG. 2: Demonstrates that body mass index (BMI, calculated using a standard formula (Weight in grams/body length in cm$^2$), and size of abdominal fat depot are decreased in PPARδ(β) heterozygous knockout mice (+/−) as compared to PPARδ(β) wild type mice (+/+). The figure also illustrates that both PPARδ(β) heterozygous knockout mice and wild type mice maintain similar body lengths over the course of the study. In this experiment mice were maintained on a high fat/high sucrose diet for 16 weeks, their length and body weight were then determined. The animals were sacrificed and abdominal fat depot removed and weighed. +/+ wild-type mice with 2 functional copies of PPARδ(β) and +/−, heterozygous knockout mice in which one PPARδ(β) gene copy is inactivated were used in this study.

Figure 3:
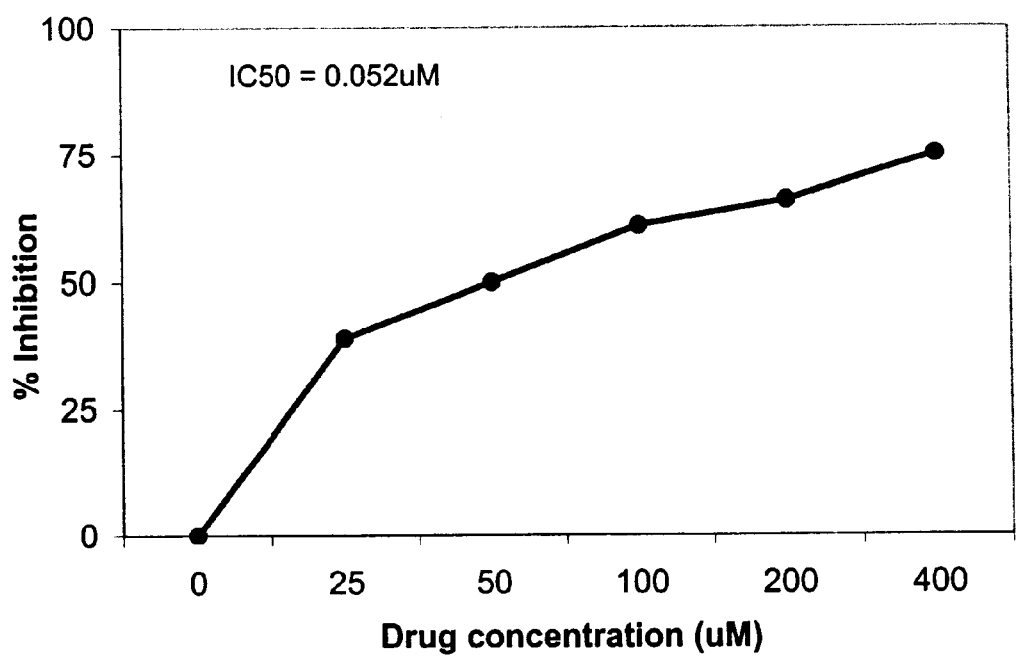

FIG. 3: Illustrates results from a PPARδ(β) ligand binding assay. In this assay non-radiolabeled L-165041 competitively inhibited in a dose dependent manner the binding $^3$H-labeled PPARδ(β) ligand (Berger et al. *J. Biol. Chem.* 274:6718–6725, 1999.) binding to PPARδ(β) LBD. The binding affinity of compound L-165041 to PPARδ(β) LBD is determined by calculating the amount of compound required for half maximal (IC50=0.052 μM) inhibition of $^3$H-labeled L-165041 (Leibowitz and Berger, WO 97/28149, 1997), binding to PPARδ(β).

Figure 4:
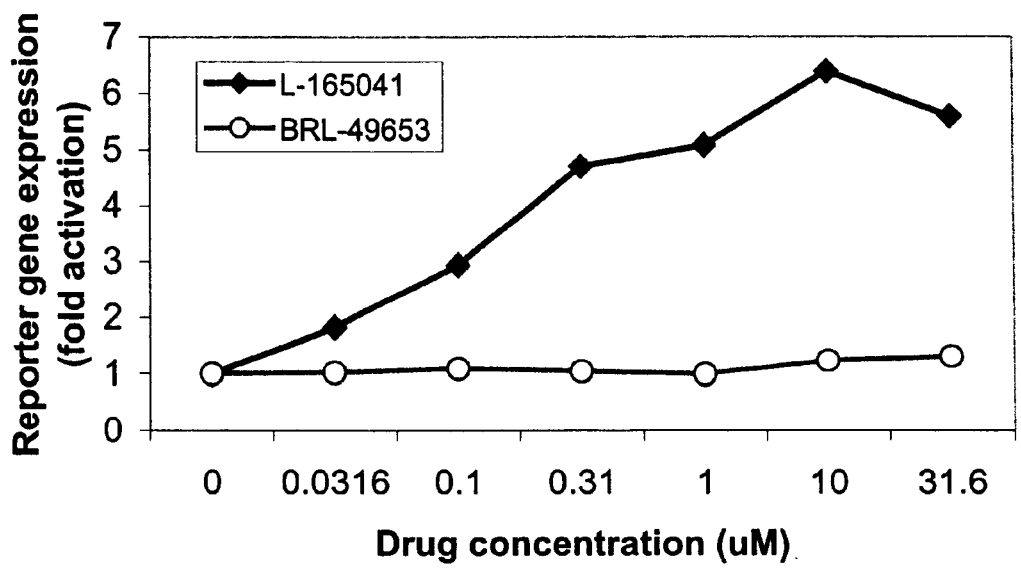

FIG. 4: Illustrates dose dependent activation of reporter gene SEAP function in CHO cells by the PPARδ(β) selective ligand L-165041 and not by the PPARγ selective ligand BRL-49653. CHO cells stably transfected with Gal4/PPARδ (β), and a Gal4 DNA response element (RE) driven SEAP reporter gene in a 96-well plate are treated separately with a PPARδ(β) selective ligand L-165041 and a PPARγ selective ligand BRL-49653.

Figure 5:
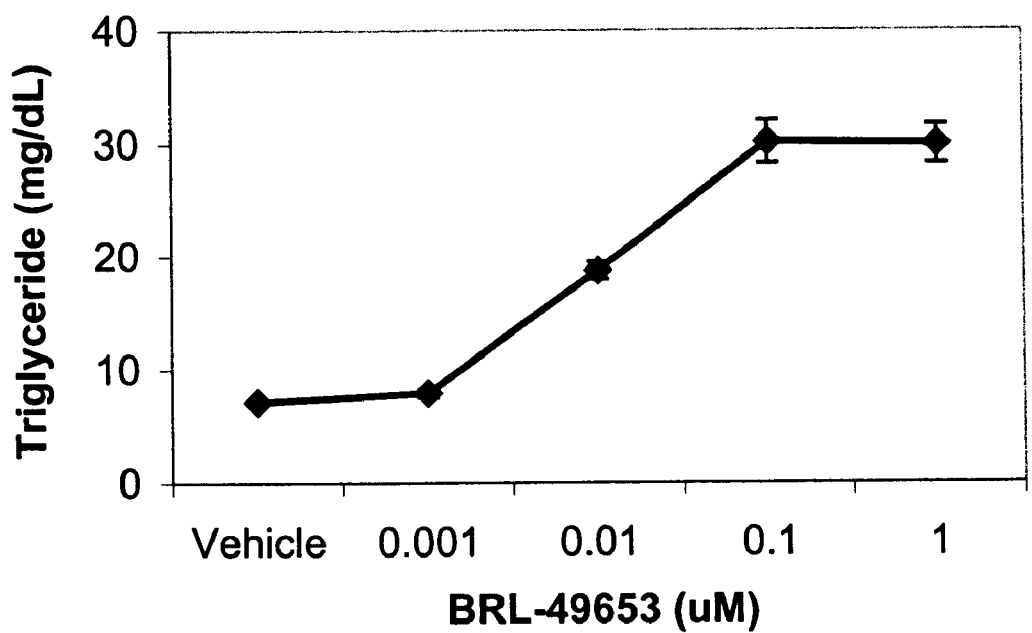

FIG. 5: Illustrates dose dependent accumulation of triglycerides in NIH 3T3L-1 pre-adipocyte in response to PPARγ selective agonist BRL-49653. The cells were treated with increasing concentration of BRL-49653.

Figure 6:
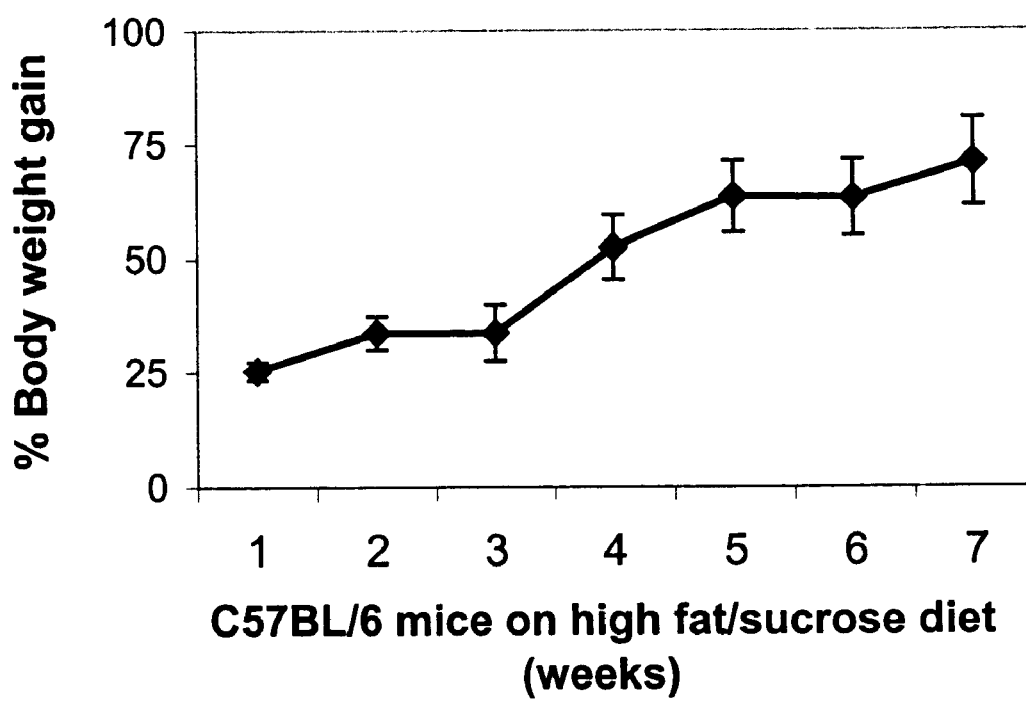

FIG. 6: Illustrates that C57BL/6 mice, when given a diet rich in fat (40%) and sucrose (40%), gain body weight steadily and become obese over a period of 7 weeks.

DETAILED DESCRIPTION OF THE INVENTION

Figure 1:
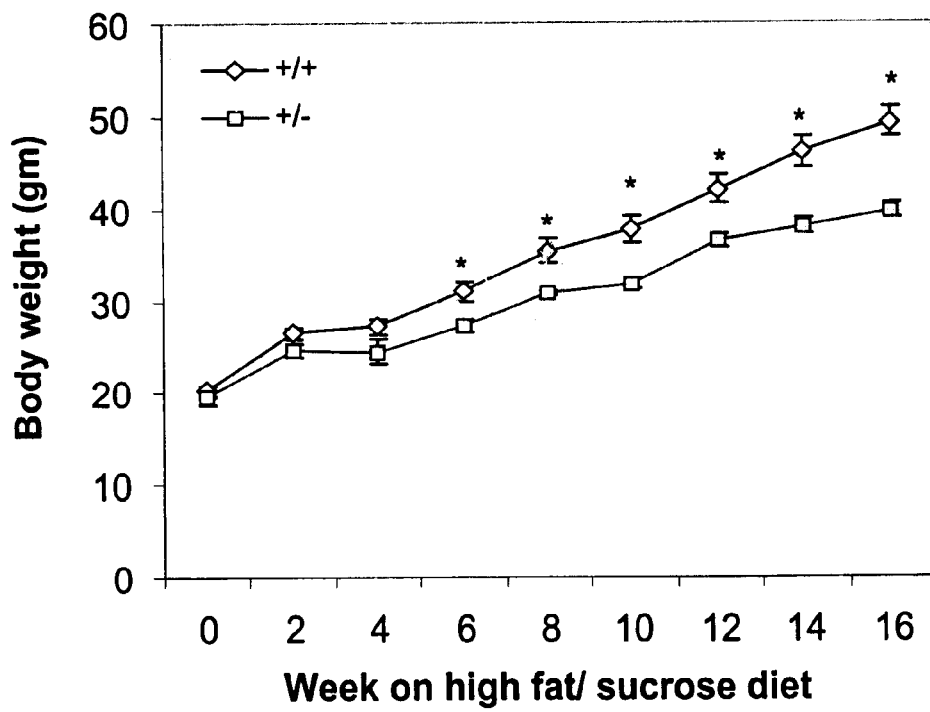
FIG. 1: Illustrates the resistance of PPARδ(β) heterozygous knockout mice to high fat/sucrose diet-induced obesity.

In mammals, most genes are represented by two functional copies. The present invention discloses for the first time the result of inactivation of one copy of the PPARδ(β) gene in mice through a gene knockout approach. PPARδ(β) heterozygous knockout mutant mice with one gene copy inactivated, exhibit no abnormal behavioral properties. They also show normal body weight as compared to wild type littermates with two gene copies when fed a regular low fat (4–6%) chow diet. However, when fed a diet rich in fat (40%) and sucrose (40%) the heterozygous knockout mice show resistance to diet-induced obesity as compared to wild type littermate control mice (FIG. 1). As illustrated in FIG. 1, PPARδ(β) heterozygous knockout mice gained body weight at a decreased rate relative to PPARδ(β) wild type mice. The heterozygous knockout mice have reduced body mass index (BMI) values, which is a measure of body fat and obesity, without significant changes in body length (FIG. 2). Anatomical analysis shows a substantial reduction in the size of the abdominal fat depot in heterozygous knockout mice relative to wild-type mice (FIG. 2). In mammals, the size of the abdominal fat depot is frequently associated with the risk for the development of insulin resistance and type 2 diabetes. In accordance with this, blood plasma chemistry analysis shows significantly reduced levels of both fasted and ad libitum fed insulin in heterozygous PPARδ(β) knockout mice as compared to wild type animals (Table 1). This finding is interpreted as an indication of increased insulin sensitivity in heterozygous PPARδ(β) knockout mice because they are able to maintain wild type levels of both fasting and fed glucose with substantially reduced levels of insulin (Table 1, below).

Another important finding in heterozygous PPARδ(β) knockout mice is that the body weight reduction is achieved without any significant change in blood plasma levels of free fatty acids, triglycerides or cholesterol during the course of the study (Table 1).

TABLE 1

| Week (on diet) | Geno-type | Glucose (mg/dL) | Insulin (ng/ml) | Cholesterol (mg/dL) | Trigly-cerides (mg/dL) | NEFA (meq/L) |
|---|---|---|---|---|---|---|
| 12 (fasted) | +/+ | 103 ± 8 | 0.87 ± 0.25 | 151 ± 12 | 118 ± 7 | 0.81 ± 0.05 |
|  | +/− | 107 ± 11 | 0.30 ± 0.0* | 125 ± 5 | 132 ± 12 | 0.8 ± 0.10 |
| 16 (fed) | +/+ | 230 ± 8 | 14.12 ± 0.84 | 218 ± 16 | 150 ± 14 | 0.48 ± 0.02 |
|  | +/− | 207 ± 7* | 4.2 ± 0.6* | 178 ± 12 | 133 ± 9 | 0.54 ± 0.06 |

*Statistically significant difference, p < 0.05

The data in this table demonstrates that PPARδ(β) heterozygous knockout mice show improved insulin sensitivity (i.e. reduced levels of fasting and fed insulin while maintaining glucose levels equal or less than that of wild type mice) relative to wild-type mice. In addition the data shows that there is no significant change in plasma lipid levels including free fatty acids, triglycerides and or cholesterol. In this study blood was collected from the tail vein after 16-hour fasting and after over night ad libitum feeding. Plasma, glucose, insulin, cholesterol, triglycerides and NEFA values were determined using standard methodologies.

The herein described invention therefore discloses that PPARδ(β) potentiates an increase in abdominal fat, obesity and insulin resistance (high insulin) when the animals are fed a diet high in fat and sucrose. However, when one copy of PPARδ(β) was inactivated as in heterozygous PPARδ(β) knockout mice, these animals show: (1) resistance to diet-induced obesity, (2) reduced abdominal fat pad mass, and (3) improvement in insulin sensitivity (reduced levels of insulin). Significantly, weight loss and reduction in abdominal fat pad mass are achieved in heterozygous PPARδ(β) knockout mice without any significant changes in blood lipid profile. The present invention therefore presents a genetic proof of principle for a method for treating obesity and the often associated insulin resistance and type 2 diabetes through some degree of inactivation of PPARδ(β).

The present invention provides a method for treating obesity, insulin resistance and type 2 diabetes in mammals through administration of a pharmacological composition containing an agent which may have the ability to reduce: (1) the activity of PPARδ(β) protein, or (2) expression of the PPARδ(β) gene, or (3) expression of PPARδ(β) regulated target genes (or any combination of the above). The inactivation of PPARδ(β) may be achieved through: (1) direct binding of a pharmacological agent (a PPARδ(β) antagonist) to the PPARδ(β) receptor and reduction of its transcriptional activation potential, or (2) through disrupting a productive association of PPARδ(β) with its obligate heterodimeric binding partner RXRα, or (3) downregulating the expression of the PPARδ(β) gene, or (4) selectively modulating its activity in a tissue through preventing the binding of a co-activator, or promoting the binding of a co-repressor, or any combination of the above. The resulting product of these changes may include any combination of (but are not limited to): (1) prevention of weight gain, (2) weight loss and (3) improvement in insulin resistance.

The present invention also provides a treatment method involving the use of a combination of a PPARδ(β) antagonist, anti-diabetic agents such as but not limited to metformin and/or a sulfonylurea to control insulin resistance and type 2 diabetes in obese insulin resistant/type 2 diabetes patients. Since most obese diabetic individuals also suffer from dyslipidemia and cardiovascular disease, this invention also proposes that a combination of a PPARδ(β) antagonist, an anti diabetic agent and a lipid lowering agent such as a PPARα agonist (such as, but not limited to, fenofibrate and gemfibrozil) and a HMG-COA reductase inhibitor (such as, but not limited to, pravastatin, lovastatin, simvastatin and atorvastatin) may be used to reduce hyperlipidemia and cardiovascular diseases.

This invention also provides methods for screening and identification of compounds that bind to and/or regulate PPARδ(β). The PPARδ(β) ligand binding domain (LBD) from a mammalian species including human and/or a non-mammalian species such as frog (Xenopus), is used for screening for compounds that bind to the LBD (Schmidt et al, *Mol. Endocrinology*, 6:1634–1641, 1992; Evans et al., Sequence XR-4 in U.S. Pat. No. 5,571,696, 1996; Berger et al. *J. Biol. Chem.*, 274:6718–6725, 1999). In this in vitro binding assay, the affinity of a test compound to PPARδ(β) is determined by its ability to competitively inhibit binding of a known ligand (as described in ref Leibowitz and Berger WO 97/28149 1997; Berger et al. *J. Biol. Chem.*, 274:6718–6725, 1999.) to PPARδ(β). In the cell based assay, a suitable mammalian, insect, or yeast cell line is co-transfected with a chimeric Gal4/PPARδ or GR/PPARδ receptors and Gal4/SEAP, Gal-4/β-lactamase and a Gal-4/luciferase or GR/SEAP, GR/β-lactamase, GR/luciferase or other suitable reporter gene DNA constructs (Sadowski and Ptashne, *Nuc. Acid. Res.* 17: 7539, 1989; Kliewer et al., *Nature*, 358:771–774, 1992; Schmidt et al, *Mol. Endocrinology*, 6:1634–1641, 1992; Lehmann et al., *J. Biol. Chem.*, 270:12953–12956, 1995; Tugwood et al., *Arch. Toxicol.*, 72:169–177, 1998; Berger et al. *J. Biol. Chem.*, 274:6718–6725, 1999;). The chimeric receptor is made up of the DNA binding domain (DBD) of yeast Gal-4 or mammalian glucocorticoid receptor (GR) transcription factors and the LBD of a mammalian or other PPARδ(β). In the reporter gene vector, a low expressing promoter (such as, but not limited to, thymidine kinase or SV-40 minimal early promoter) is coupled to a Gal-4 or GR DNA response element or multiple copies thereof, and will direct the expression of secreted alkaline phosphatase (SEAP), β-lactamase, or luciferase and/or another suitable reporter gene. According to this cell-based assay, the chimeric receptor binds to the DNA response element in the promoter through the Gal-4 or GR DBD and regulates expression of the reporter gene as a function of binding of a ligand(s) to the PPARδ(β) LBD. Compounds that inactivate (antagonists) or activate (agonists) reporter gene expression will be selected on the basis of this assay for further biological testing.

In another approach, any established cell line that maintain expression of endogenous PPARδ(β) are transfected with the PPARδ(β) selective DNA response element (the PPRE), a directed reporter gene (such as but not limited to) SEAP, β-lactamase or luciferase (see He et al., *Cell*, 99:335–345, 1999; Mano et al., *J. Biol. Chem.*, 275:8126–8132, 2000). In this cell-based assay, the endogenous PPARδ(β) will bind to the PPARδ(β) PPRE on the promoter and regulate expression of the reporter gene as a function of ligand binding to the PPARδ(β) LBD. Compounds that inactivate (antagonists) or activate (agonists) will be selected on the basis of this assay for further biological testing.

Most pre-adipocyte cells (cultured cells) and human, primate and rodent primary adipocytes are capable of differentiating into mature adipocytes after induction by hormones and pharmaceutical agents. These hormones and agents may include (but are not limited to) insulin, dexamethasone, 3-isobutyl-1-methyl-xanthine (IBMX), long chain fatty acids, thiazolidinediones, prostaglandins, leukotrienes, eicosanoids, retinoids, RXRα agonists and any suitable combinations of all of the above (Kohanski et al., *J. Biol. Chem.*, 261:12272–12281, 1986; Brun et al., *Genes. Dev.*, 10:974–984, 1996). The selected PPARδ(β) regulators (antagonists) are further investigated for their ability to mediate pre-adipocyte differentiation into adipocytes as measured by: (1) triglyceride accumulation, and/or (2) the expression of various marker genes such as aP2, adipsin, lipoprotein lipase or fatty acid synthase.

Candidate PPARδ(β) antagonist compounds identified through one or more of the in vitro screening assays described above are then administered to well known animal models such as, but not limited to, genetically or diet-induced obese mice (ob/ob, db/db, KkAy, agouti, high fat diet induced obese C57BL/6 or others), rats (fa/fa, ZDF, or others), hamsters (high fat diet induced obese Golden Syrian or other suitable strains) or monkeys (high fat diet induced obese cynamologous or African Green monkey) (see York {Genetic models of obesity} and Sclafani (Dietary models of obesity}, both in Obesity, Bjorntorp and Brodoff eds. JB Lippincott Company, 1992; McIntosh and Pederson, McNeill. eds CRC press LLC, 337–398, 1999). Alternatively, these animals may also be used as primary screening tools. Compounds are administered in a pharmacologically acceptable vehicle to animals by intravenous, subcutaneous or intraportal injection, orally, or mixed with food or water, acutely or over an extended period of time. During the course of the study, various parameters such as water and food consumption, body weight gain and body temperature, are measured. Through tail vein bleeding blood is collected and plasma analyzed for glucose, insulin, free fatty acids, triglycerides and cholesterol. The animals are also tested for glucose tolerance and insulin sensitivity. The treated animals may also be scanned as compared to untreated obese animals for improvement in osteoarthritis of the joints. Compounds that act to reduce body weight or decrease plasma glucose and lipid levels or show increased glucose tolerance and insulin sensitivity and/or improvement in osteoarthritis of the joints are then selected for further study.

The invention described herein also includes pharmaceutically acceptable compositions of a PPARδ(β) antagonist for synthesis, storage, and delivery to a mammal (including humans) for the treatment of obesity and insulin resistance.

Many assays known to those skilled in the art of molecular biology, biochemistry, genetics, pharmacology and in vivo physiology can be used to screen and discover compounds that regulate PPARδ(β) activity, regulate pre-adipocyte differentiation and prevent or ameliorate obesity, insulin resistance, and dys-metabolic syndrome. Several exemplary assays are disclosed below.

EXAMPLE 1

In Vitro Binding Assay

A single *E.coli* colony containing His-tagged PPARδ(β) LBD (amino acid 139–441, Schmidt et al., *Mol. Endocrinology*, 6:1634–1641, 1992) expressing plasmid DNA is mixed with 3 ml Luria broth (LB) supplemented with 100 μg/ml antibiotic ampicilin and grown at 37° C. PPARδ(β) LBD protein expression is induced with IPTG (added to 0.4 mM final concentration). Bacterial pellet from 1 liter culture is resuspended in 50 ml of buffer containing 20 mM Hepes (pH 7.8), 100 mM NaCl, 1 mM DTT and 1 Complete™ protease inhibitor cocktail tablet (Boehringer Mannheim) and lysed by sonication. The lysate is centrifuged at 10,000 rpm for 30 minutes and the supernatant is used for ligand binding assay. For each binding assay point in a 96 well plate, 37 μg bacterial lysate is mixed with 50 nM of a $^3$H-labeled PPARδ(β) selective ligand (Compound F in Leibowitz and Berger, WO 97/28149, 1997; L-165041 in Berger et al. *J. Biol. Chem.* 274:6718–6725, 1999) in a buffer containing 20 mM Tris-HCl (pH 8.0), 150 mM NaCl, 0.5% BSA, and 0.5% Chaps and 333 μg Yttrium silicate copper his-tag SPA beads (Amersham) and incubated in a Packard 96 well Optiplate. Non-radiolabeled L-165041 in DMSO solution is added to a desired final concentration to the reaction buffer and further incubated at room temperature for 1 hour. The plates are then read on Packard top-count beta-scintillation counter (1 minute/well). The binding affinity of L-165041 to PPARδ(β) LBD is determined by calculating the amount of compound required for half maximal (IC50=0.052 μM) inhibition/displacement of $^3$H labeled PPARδ(β) ligand (compound F in Leibowitz and Berger, WO 97/28149, 1997) binding to PPARδ(β) protein (FIG. 3). In this binding assay any test compound may replace L-165041 and the binding affinity for PPARδ(β) is easily determined.

EXAMPLE 2

Cell Based Transactivation Assay

CHO cells, stably transfected with a chimeric receptor construct made of yeast Gal4 DBD (amino acid 1–144; {Sadowski and Ptashne, *Nuc. Acid. Res.* 17:7539, 1989}) fused to human PPARδ(β) LBD (amino acid 139–441; {Schmidt et al, *Mol. Endocrinology*, 6:1634–1641, 1992}) and a Gal4 DNA response element (RE) driven secreted alkaline phosphatase (SEAP) reporter gene is grown in DMEM medium supplemented with 10% fetal calf serum and antibiotics Geneticin and Zeocin (400 μg each) in 96 well plates.

PPARδ(β) selective agonist L-165041 is added (31600, 10000, 1000, 31.6, 10, 3.16 nM or other suitable concentrations in 0.5% DMSO containing media) to determine dose dependent induction of reporter gene activity in this cell line and PPARγ selective ligand BRL-49653 (Lehmann et al., *J. Biol. Chem.* 270:12953–12956, 1995) is used as a negative control. As illustrated in FIG. 4, L-165041 dose dependently induced reporter gene activity while PPARγ selective ligand BRL-49653 showed no induction. To this cell based assay test compounds may be added to varying concentrations in presence of L-165041. The ability of the test compound to competitively inhibit (antagonist) reporter gene activation by L-165041 (half-maximal inhibition of activation, EC50 in μM) is calculated.

TABLE 2

Assay test data for Compound A (α, β thiazolidinedione-substituted carboxylic acid) and Compound B (2-azo-benzimidazole derivative).

|  | Compound A | Compound B |
|---|---|---|
| IC50 for binding (μM) | δ = 3.8<br>α > 25<br>λ > 25 | δ = 4.7<br>α > 25<br>λ > 25 |
| ED50 for δ antagonism (μM) | 8.47 | 0.26 |
| Activity in δ, α, γ agonist assay | inactive | inactive |

EXAMPLE 3

Adipocyte Differentiation Assay

In yet another embodiment, the ability of PPARδ(β) antagonists to regulate differentiation of mouse pre-adipocyte cell lines such as NIH 3T3-L1 into mature adipocytes and accumulate lipids in the form of triglycerides in presence of hormonal signals may be determined. As an example, 1.0×10$^4$ 3T3 L1 cells per well are plated and grown to confluency in a 24 well plate in DMEM-high medium and 10% fetal bovine serum. Cells are induced to differentiate for 48 hr after adding hormonal cocktail (1 μM dexamathasone, 5 μg/ml insulin, and 0.6 μM IBMX {Kohanski et al., *J. Biol. Chem.* 261:12272–12281, 1986; Brun et al., *Genes. Dev.* 10:974–984, 1996}) to the medium. At this time, agents that further induce differentiation such as BRL-49653, a proven PPARγ agonist (Lehmann et al., *J. Biol. Chem.* 270: 12953–12956, 1995), is added (0.01 to 10 μM or other suitable concentrations in 0.5% DMSO containing media) into each well. After 24–72 hours cells are washed with PBS and lysed in 100 μL PBS containing 1% triton per well for 20 min. at room temperature. Triglyceride content is determined in cell lysates using triglyceride reagent test kit in a COBAS-MIRA instrument. As illustrated in (FIG. 5) BRL-49653 induced significant triglyceride accumulation in cells indicating induction of differentiation. This pre-adipocyte differentiation assay can be easily adapted to test for the ability of PPARδ(β) antagonists to regulate differentiation and triglyceride accumulation induced by hormonal cocktail and or BRL-49653.

EXAMPLE 4

In Vivo Obese Animal Model

In another preferred embodiment of the present invention C57BL/6 mice are fed a diet rich in fat (40%) and sucrose (40%) (see, York {Genetic models of obesity} and Sclafani (Dietary models of obesity}, both in *Obesity*, Bjorntorp and Brodoff eds. J B Lippincott Company, 1992; McIntosh and Pederson; McNeill. eds. CRC press LLC, 337–398, 1999; Farrelly et al., *Proc. Natl. Acad. Sci.* 96:14511–14516, 1999). Under these dietary conditions, C57BL/6 mice gain considerable body weight (FIG. 6) and become obese. These mice may be treated with PPARδ(β) antagonists (dose 1 to 100 mg/kg/day), administered in a pharmacologically acceptable vehicle (e.g. but not limited to 5% CM-cellulose) through intravenous, subcutaneous or intraportal injection, orally, or mixed with food or water, acutely or over an extended period of time. During the course of the study, various parameters such as water and food consumption, body weight gain, body temperature is measured by standard methods. Through tail vein bleeding, blood is collected in heparin-EDTA coated tubes to prevent clotting and blood plasma was separated and analyzed for glucose, free fatty acids, triglycerides and cholesterol using reagent kits available from Roche Diagnostics in a COBAS-MIRA instrument. Insulin and leptin are measured by commercially available ELISA kits. The animals are also tested for glucose tolerance and insulin sensitivity. This is performed by injecting a pre-determined dose of insulin (0.5 Units/kg in saline) or glucose (1 gm/kg in saline) and changes in glucose levels are monitored by tail vein bleed every 30 minutes. The compounds that lead to decreased levels of glucose after insulin injection and after a glucose load are considered insulin-sensitizing glucose lowering agents. Compounds that act to reduce body weight and or decrease glucose; lipid or show increased glucose tolerance and insulin sensitivity are selected. The treated animals may also be scanned using suitable instruments for improvement in osteoarthritis of the joints.

Test compounds that prevent or ameliorate obesity, insulin resistance, are also tested in the disease models described above, in combination with an anti diabetic agent such as but not limited to metformin and sulfonylurea and/or a lipid lowering agent such as PPARα agonists (such as, but not limited to fenofibrate and gemfibrozil) and/or HMG CoA reductase inhibitors (such as, but not limited to pravastatin, lovastatin, simvastatin and atorvastatin). During the course of the study various parameters such as water and food consumption, body weight gain, body temperature and plasma glucose, insulin, free fatty acids, triglycerides and cholesterol levels are measured. The animals are also tested for glucose tolerance and insulin sensitivity. Compounds that act to reduce body weight and or decrease glucose, lipid, or show increased glucose tolerance and insulin sensitivity are selected for further characterization.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In addition, materials, methods, and examples are illustrative only and are not intended to be limiting.

As used herein, the phrase "therapeutically effective" is intended to include an amount of a compound, or an amount of a combination of compounds, claimed effective to inhibit PPARδ(β) activity and/or treat obesity, insulin resistance and/or hyperlipidemia.

As used herein, the term "prodrug(s)" is intended to include any covalently bonded carriers which release an active parent drug of the present invention in vivo when such a prodrug is administered to a mammalian subject. Prodrugs of the present invention are prepared by modifying functional groups present in the compound in such a way that the modifications are cleaved, either in routine manipulation or in vivo, resulting in the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

As used herein, the phrase "pharmaceutically acceptable" is employed to refer to those compounds, materials, compositions and/or dosage forms which are, within the scope of sound medical judgment, suitable for use in contact with the tissues of mammals, including human beings, without excessive toxicity, irritation, allergic response, or other problem or complication commensurate with a reasonable benefit/risk ratio.

As used herein, the phrase "anti-diabetic agent" refers to a compound that will improve insulin resistance and decrease plasma glucose levels in patients with diabetes. Representative compounds within the scope of the present invention include but are not limited to metformin, rosiglitazone, and pioglitazone.

As used herein, the phrase "lipid-lowering agent" refers to a compound that will lower plasma lipid levels—cholesterol and triglycerides, in patients suffering from hyperlipidemia and/or cardiovascular disease. Representative compounds within the scope of the present invention include but are not limited to pravastatin, simvastatin, atorvastatin, and gemfibrozil.

As used herein, the phrase "administered in combination", and the terms "combination" or "combined" when referring to compounds, components, or compositions described herein, means the compounds, components, or compositions are administered concurrently to the mammal being treated. When administered in combination each compound, component, or composition may be administered in any order at the same time or sequentially in any order or at different points in time, so as to provide the desired therapeutic effect.

As used herein the terms "modulate or modulates" refer to an increase or decrease in the amount, quality or effect of a particular activity or protein.

Dosage And Formulation

A suitable PPARδ(β) antagonist compound can be administered to patients to treat obesity and other metabolic disorders as the compound alone and/or mixed with an acceptable carrier in the form of pharmaceutical formulations. Those skilled in the art of obesity, insulin resistance and hyperlipidemia can easily determine the dosage and route of administration of the compound to mammals, including humans, in need of such treatment. The route of administration may include but is not limited to oral, rectal, transdermal, buccal, subcutaneous, intramuscular, intradermal, intravenouos, or intestinal administration. The compound is formulated according to the route of administration based on acceptable pharmacy practice (Fingl et al., in *The Pharmacological Basis of Therapeutics*, Ch. 1, p. 1, 1975; *Remington's Pharmaceutical Sciences*, 18th ed., Mack Publishing Co, Easton, Pa., 1990).

In combination therapy, the dose and route of administration of the second or third drug (anti-diabetic or lipid lowering drugs) will depend on the drug chosen and the severity of insulin resistance, type 2 diabetes and/or hyperlipidemia.

The pharmaceutically acceptable PPARδ(β) antagonist composition of the present invention can be administered in such oral dosage forms as tablets, capsules (each of which includes sustained release or timed release formulations), pills, powders, granules, elixirs, tinctures, suspensions, syrups, and emulsions. The composition of the present invention can also be administered in intravenous (bolus or infusion), intraperitoneal, subcutaneous, or intramuscular form, all using dosage forms well known to those of ordinary skill in the pharmaceutical arts. The composition may be administered alone, but generally will be administered with a pharmaceutical carrier selected on the basis of the chosen route of administration and standard pharmaceutical practice.

The dosage regimen for the composition of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. The composition of this invention may be administered in a single daily dose, or the total daily dosage may be administered in divided doses of two, three, or four times daily.

The composition of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The composition is typically administered in a mixture with suitable pharmaceutical diluents, excipients, or carriers (collectively referred to herein as pharmaceutical carriers) suitably selected with respect to the intended form of administration, that is, oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as ethanol, glycerol, and water. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrators include, but are not limited to, starch, methyl cellulose, agar, bentonite, and xanthan gum.

The composition of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same and compositions containing the same.

The compositions of the present invention may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the composition of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company, 1995, a standard reference text in this field Representative useful pharmaceutical dosage forms for administration of the compound of this invention can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate;

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Obviously, numerous modifications and variations of the present invention are possible in light of the above teachings. It is therefore understood that within the scope of the appended claims, the invention may be practiced otherwise than as specifically described herein.

The present invention is not to be limited in scope by the specific embodiments described that are intended as single illustrations of individual aspects of the invention. Functionally equivalent methods and components in addition to those shown and described herein will become apparent to those skilled in the art from the foregoing description and accompanying drawings. Such modifications are intended to fall within the scope of the appended claims.

What is claimed is:

1. A method for treating obesity in a mammal comprising administering to said mammal a therapeutically effective amount of a compound or a pharmaceutical composition that inhibits PPARδ(β) activity and reducing the obesity in said mammal.

2. A method according to claim 1, wherein said mammal is a human.

3. A method for treating obesity, insulin resistance and dyslipidemia in an obese mammal comprising administering to said mammal a therapeutically effective amount of a compound or a pharmaceutical composition that inhibits PPARδ(β) activity in combination with an anitdiabetic agent and/or lipid-lowering agent and reducing the obesity in said mammal.

4. A method according to claim 3, wherein said mammal is a human.

* * * * *